US009735896B2

(12) United States Patent
Flippo et al.

(10) Patent No.: US 9,735,896 B2
(45) Date of Patent: Aug. 15, 2017

(54) EMERGENCY RESPONSE SYSTEMS AND METHODS

(71) Applicant: Integrity Tracking, LLC, Boca Raton, FL (US)

(72) Inventors: Robert Flippo, Boca Raton, FL (US); Jean Robichaud, Boca Raton, FL (US); Chris A. Otto, Huntsville, AL (US)

(73) Assignee: Integrity Tracking, LLC, Boca Raton, FL (US)

( * ) Notice: Subject to any disclaimer, the term of this patent is extended or adjusted under 35 U.S.C. 154(b) by 0 days.

(21) Appl. No.: 14/157,510

(22) Filed: Jan. 16, 2014

(65) Prior Publication Data

US 2014/0199946 A1   Jul. 17, 2014

Related U.S. Application Data

(60) Provisional application No. 61/753,198, filed on Jan. 16, 2013.

(51) Int. Cl.
| | | |
|---|---|---|
| *H04B 17/00* | (2015.01) | |
| *G08B 25/01* | (2006.01) | |
| *A61B 5/00* | (2006.01) | |
| *H04W 76/00* | (2009.01) | |
| *H04W 4/22* | (2009.01) | |
| *G08B 25/00* | (2006.01) | |

(52) U.S. Cl.
CPC ....... *H04B 17/0085* (2013.01); *A61B 5/0022* (2013.01); *G08B 25/016* (2013.01); *H04W 76/007* (2013.01); *G08B 25/009* (2013.01); *H04W 4/22* (2013.01)

(58) Field of Classification Search
CPC ....... H04B 17/00–17/19; G08B 25/016; G08B 25/009; H04W 76/007; A61B 5/0022
See application file for complete search history.

(56) References Cited

U.S. PATENT DOCUMENTS

| | | | |
|---|---|---|---|
| 3,787,626 A * | 1/1974 | Subieta ................ | H04M 1/573 379/142.01 |
| 6,571,279 B1 * | 5/2003 | Herz et al. .................... | 709/217 |
| 8,737,571 B1 * | 5/2014 | Seeley et al. ................ | 379/1.03 |
| 2003/0177222 A1 * | 9/2003 | Bradley et al. ............... | 709/224 |
| 2006/0146783 A1 * | 7/2006 | Yurchenko ..................... | 370/351 |
| 2006/0176167 A1 * | 8/2006 | Dohrmann ..................... | 340/506 |
| 2009/0181638 A1 * | 7/2009 | Gottlieb ..................... | 455/404.1 |
| 2009/0227223 A1 * | 9/2009 | Jenkins ...................... | 455/404.1 |
| 2014/0105061 A1 * | 4/2014 | Kannan ........................ | 370/254 |

* cited by examiner

*Primary Examiner* — Gennadiy Tsvey
(74) *Attorney, Agent, or Firm* — Ann I. Dennen

(57) ABSTRACT

The present disclosure is an emergency response system that has a wearable device that receives an input from a user and transmits data indicative of the input. In addition, the system has a base station communicatively coupled to the wearable device that receives the data indicative of the input and transmits a test signal requesting a test be performed. Further, the system comprises logic that receives the test signal and initiates a call to the base station based upon the test signal.

53 Claims, 8 Drawing Sheets

EMERGENCY RESPONSE SYSTEMS AND METHODS

CROSS-REFERENCE TO RELATED APPLICATION

This application claims priority to U.S. Patent Application No. 61/753,198 entitled Self Test Emergency Response Systems and Methods filed Jan. 16, 2013, which is incorporated herein by reference in its entirety.

BACKGROUND

Personal Emergency Response Systems (PERS) are used in the field of medical alarms, emergency response, and telehealth monitoring. A typical PERS is used for providing fast response to elderly in need of medical assistance. For example, some PERS consist of a wearable pendant with a button for signaling help. The systems are typically characterized by a base station that resides in the home providing connectivity to the service provider via a hard wired phone line connection (via a public switched telephone network (PSTN)).

Some PERS systems include a wearable pendant, a base station or console device, a PSTN or mobile network, centralized receiver or servers for communicating with alarm devices, automated security software, and/or emergency response operators. In such a system, the pieces must all work together seamlessly to deliver an emergency response application. User accounts must be configured correctly and paired with the appropriate hardware components. In the case of a mobile medical alarm, the system must also communicate with a mobile network and subscriber identity module (SIM) card must be configured and paired correctly. If any of these components do not work, the application will not work.

Consequently, many PERS systems are installed by trained professionals that can test the system and confirm its correct operation. This is cumbersome and difficult to coordinate and also difficult to scale without having a fleet of installers across all regions the units will be sold. In addition, it uses expensive people resources to provide the installation.

SUMMARY

The present disclosure is an emergency response system that has a wearable device that receives an input from a user and transmits data indicative of the input. In addition, the system has a base station communicatively coupled to the wearable device that receives the data indicative of the input and transmits a test signal requesting a test be performed. Further, the system comprises logic that receives the test signal and initiates a call to the base station based upon the test signal.

A emergency response method of the present disclosure may comprise the following steps: receiving an input from a user via a wearable device; transmitting data indicative of the input; receiving the data indicative of the input by a base station communicatively coupled to the wearable device; transmitting a test signal requesting a test be performed; receiving the test signal; and initiating a call to the base station, based upon the received test signal.

BRIEF DESCRIPTION OF THE DRAWINGS

The present disclosure is described with reference to the accompanying drawings. The systems and methods described can be better understood with reference to the following drawings. The elements of the drawings are not necessarily to scale relative to each other, emphasis instead being placed upon clearly illustrating the principles of the invention. Furthermore, like reference numerals designate corresponding parts throughout the several views.

DETAILED DESCRIPTION

The present disclosure relates to personal emergency response systems (PERS) that may be employed for monitoring a user when the user is located at his residence in close proximity to base monitoring equipment or when the user is using cellular and/or mobile monitoring equipment but is still within fairly close proximity to the base monitoring equipment. Hardware for implementing the PERS may be installed by an installer, for example, at the user's residence, and the installer further may configure corresponding software and/or firmware of the PERS so that the PERS operates as needed for the particular user.

Thus, the PERS of the present disclosure is installed manually. Such manual installation makes the process of setting up a user prone to human error, even if installed by trained technicians. The exemplary PERS of the present disclosure performs automated self test systems and methods so that proper operation is verified in a predictable and automated fashion. While not limited to a mobile PERS architecture, which is described with reference to FIG. 2, the present disclosure describes systems and methods for facilitating automatic test of equipment to assure proper operation in absence of a trained professional installer. Such a system is easier to install, less error prone and more scalable.

Figure 1:
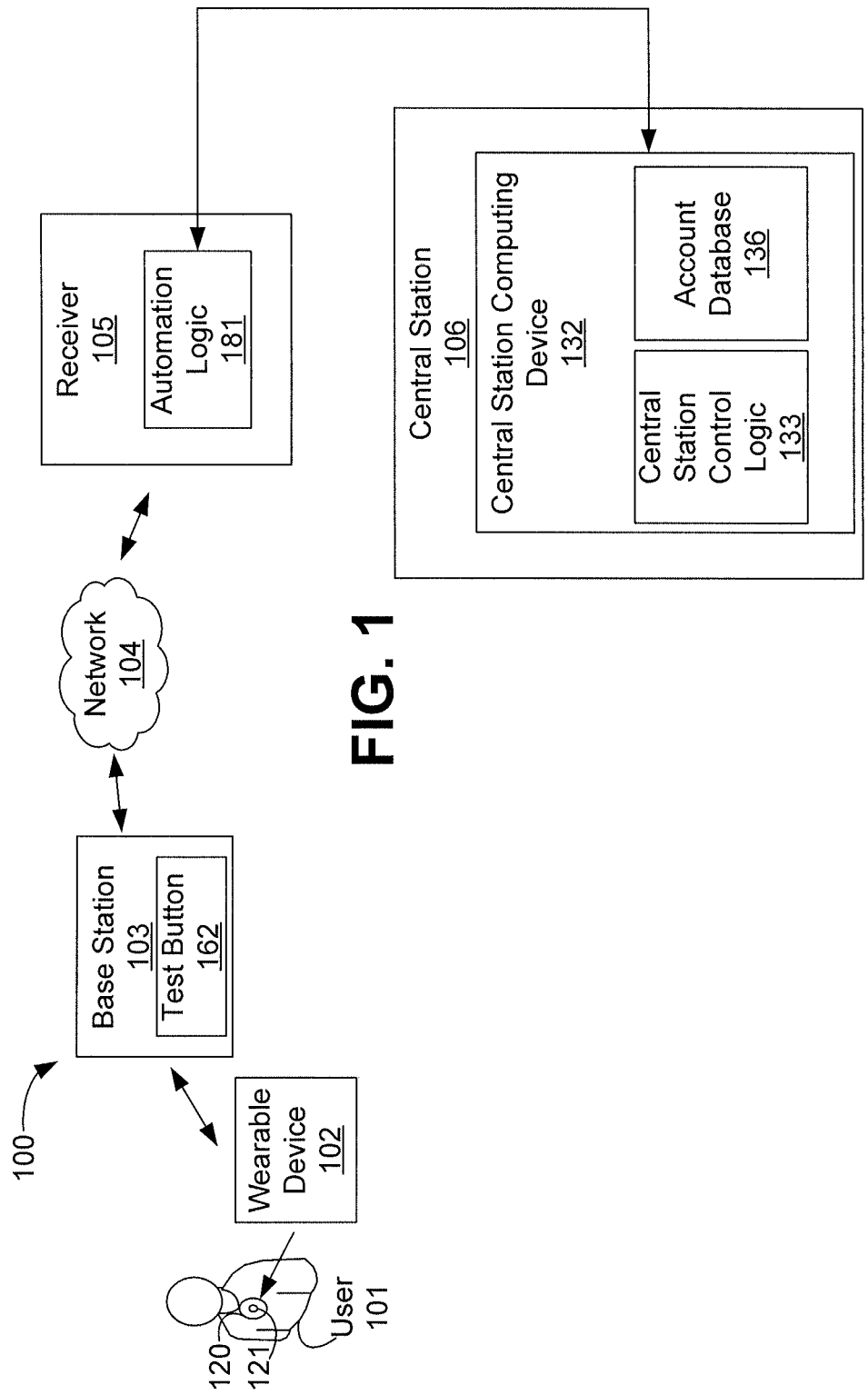
FIG. 1 is a block diagram depicting an exemplary personal emergency response system (PERS) in accordance with an embodiment of the present disclosure.

FIG. 1 depicts an exemplary embodiment of a personal emergency response system 100 for monitoring a user 101 (hereinafter referred to as the "monitored user 101") that is within short wireless range from a base station 103 (e.g. less than 1,000 feet). In such an embodiment, the monitored user 101 dons a wearable device 102, which communicates with the base station 103. The user 101 may move short distances away from the base station 103 (within his or her home for example), and the wearable device 102 continues to communicate with the base station 103.

In one embodiment, the base station 103 comprises a test button 162. The user 101 or a service technician installing the system 100 may select the test button 162 in order to test working operation of the system 100.

Note that the distance from which the monitored user 101 may travel away from the base station 103 depends upon the communication characteristics, e.g., the strength of the transceivers used in the wearable device 102 or base station 103. As a mere example, the monitored user 101 may desire to go into his/her yard (not shown) to perform yard work. In such an example, the monitored user 101 wears the wearable device 102 and although he/she is remote from the base station 103, the wearable device 102 continues to be available for actuation by the monitored user 101 in the event of an emergency wherein the monitored user 101 needs and/or desires assistance.

As shown in FIG. 1, the system 100 further comprises a central station 106 and a central station computing device 132. The central station computing device 132 is communicatively coupled to the wearable device 102 via a number of components, including the network 104.

In one embodiment, the wearable device 102 is communicatively coupled to the base station 103, as described hereinabove, which is communicatively coupled to a receiver 105 via the network 104. The receiver 105 may be any type of device that receives or places private branch exchange (PBX) or wired calls via the network 104. Notably, the receiver is communicatively coupled to the central station computing device 132 located at the central station 106.

In one embodiment, the receiver 105 comprises automation logic 181, which is described further herein. The automation logic 181 receives and transmits information, e.g., data, received from a connected call to the central station computing device 132.

In one embodiment, the network 104 is a public switched telephone network (PSTN). The PSTN is communicatively coupled to the base station 103 via a telephone line (not shown). During operation, the base station 103 transmits data indicative of information received from the wearable device 102 via the network 104 to the receiver 105, which is in turn transmitted to the central station computing device 132. Note that other types of networks may be employed in other embodiments, as described further herein.

In one embodiment, the wearable device 102 may be a pendant such as is shown on the monitored user 101 in FIG. 1. Note that the wearable device 102 may be any type of device that may be worn and/or carried by the monitored user 101 that is configured to communicate with the base station 103.

In one embodiment, the wearable device 102 comprises an emergency response button 120. As described hereinabove, the wearable device 102 may be the pendant as shown, and the button 120 is configured and arranged for accessible depression by monitored user 101. Thus, as an example, if the monitored user 101 falls while remote from the base station 103, the user presses the button 120 to request help, which is described further herein.

The wearable device 102 is communicatively coupled to the base station 103 via a wireless connection wherein a digital radio protocol is employed for communication. In one embodiment, the protocol employed may be ZigBee, Z-wave, and Wi-Fi, for example. Any type of protocol known in the art or future-developed may be used in other embodiments. In one embodiment, a very simple Amplitude Shift Keyed (ASK) modulation at 315 MHz or 433 MHz is employed, and lower frequencies are used so that permeation and transmission of signals in and through structures, e.g., building walls, is more effective.

In one embodiment, when the monitored user 101 presses the button 120, the wearable device 102 transmits a signal to the base station 103. In such embodiment, the signal contains information indicative of a unique identifier (UID) that identifies the wearable device 102. Further, the signal contains information indicative of a button press (hereinafter referred to as an "event").

In some embodiments of the wearable device 102, the wearable device 102 may comprise a different type of device that may be actuated or otherwise activated that initiates the signal that the wearable device 102 transmits to the base station 103. The button 120 configured and arranged on the pendant, as shown, is merely an exemplary embodiment of a wearable device 102.

In response to receipt of the signal, the base station 103 follows an emergency response protocol. In one embodiment, the base station 103 processes the signal received from the wearable device 102 to determine if an existing alarm is currently in progress, e.g., the monitored user 101 previously selected the button 120.

Determination of an existing alarm may be performed using various methods. For example, the base station 103 may store dynamic information indicating that an alarm is active and make a determination based upon the dynamic information. In another example, the base station 103 may query the central station computing device 132 via the network 104. In this regard, the central station computing device 132 may store information indicating that an alarm is active. In response, the central station computing device 132 may respond to the query indicating whether an alarm is active.

If no alarm is currently in progress, the base station 103 activates an audible and/or visual indication, for example, that an alarm is active. Typically the audible or visible alarm emanates from the base station 103; however the alarm may emanate from other devices or components within the system 100 in other embodiments.

In response to the monitored user 101 actuating the button 120, the base station 103 seizes a connected telephone line (not shown) that connects the base station 103 to the network 104 and dials a number for connecting the base station 103 to the receiver 105 and inevitably to the central station computing device 132. Note that in one embodiment, the base station 103 may be provisioned in advance with a number of the central station 106 prior to shipment or a technician may provision the number to be called upon installation of the equipment at the monitored user's residence or the accommodations in which the equipment is intended to be used, as described hereinabove.

When the base station 103 places a call to the central station 106, the call is received by the receiver 105. In this regard, if the call is successful, the base station 103 conveys information, e.g., data indicative of the phone number of the calling equipment or data indicative of the hardware of the base station 103 through the automation logic 181 to the central station computing device 132. In addition to identifying information, e.g., a telephone number or hardware identifier, the base station 103 may convey over the connected line data describing the alarm. As an example, the base station 103 may transmit data indicative of a user account identifier and/or the type of alarm. Further, the base station 103 may transmit a hardware identifier that identifies, for example, the wearable device 102 or the base station 103. Upon receipt of the call from the base station 103 and receipt of the data by the receiver 105, the automation logic 181 transmits the received data to the central station computing device 132, which is received and processed by the central station control logic 133. Note that in one embodiment wherein the base station 103 transmits a hardware identifier, the central station control logic 133 uses the hardware identifier to determine other data associated with the monitored user 101 associated with the hardware identifier, which is described further herein. This may also be the case with respect to receipt of a phone number. An account database 136 may store account information, including the user's name, address, hardware identifiers, phone numbers, etc. The central station control logic 133 may use one piece of this data to identify other data to which it is correlated.

During operation, the monitored user 101 may actuate the button or the wearable device 102 (or base station 103) may detect circumstances that warrant follow up by a live central station attendant. In such a scenario, information or data transmitted to the central station computing device 132 from the base station 103 in response to that described is hereinafter referred to as "event data," which is data transmitted to the central station computing device 132 by the base station 103 in response to an event.

Note that the one type of protocol that may be used for communication to the central station receiver 105 is the Contact ID Protocol by Ademco®. This protocol describes a data transmission protocol encoded using ordinary dual tone multi-frequency (DTMF) tones. Other protocols exist that utilize DTMF tones and may be used as well. For purposes of the present disclosure, any protocol may be used in other embodiments, including DTMF-based transmission or other tones or even using a facsimile (FAX) or modulator-demodulator (MODEM) transmission as described in U.S. patent application Ser. No. 13/539,296 entitled Personal Monitoring System and Method, which is fully incorporated herein by reference in its entirety.

The receiver 105, such as an Osborne Hoffman receiver, answers the call placed by the base station 103 and process the data received. The receiver 105 communicates with the automation logic 181, such as General Electric (GE) Mastermind®, DICE, or Stages. The enumerated examples of automation software is for exemplary purposes, and other automation software, or any type of logic that effectuates transmitting received data to the central station computing device 132, may be used in other embodiments.

In one embodiment, upon receipt of a message from the automation logic 181, which may contain data, for example, the phone number or a hardware identifier that is contained in the data transmitted from the base station 103 that originated the phone call, the central station control logic 133 may locate in the account database 136 residing on the central station computing device 132 other information corresponding to the phone number identified in the message from the automation logic 181. In this regard, the central station control logic 133 accesses the associated user's account record (based upon the identifier in the data received or the number of the line that originates the call) and queues the alarm for servicing by a central station operator at the central station 106. This is referred to as "call binding," which means associating a call with a subscriber account. Note that in the system 100 depicted in FIG. 1, the base station 103 is "wired" to the receiver 105 via the network 104. In one embodiment depicted in FIG. 2, the base station 103 is described as a cellular base station. In such a scenario, which shall be described further herein with reference to FIG. 2, data is transmitted substantially wirelessly over a data channel and receipt of a call (or an alarm, for example) is managed as described with reference to FIG. 2.

When an operator is available for handling the event, the operator accepts the alarm and connects an audio talk path to the base station 103. Note that in one embodiment, the initiation of the audio talk path may be initiated automatically by the central station computing device 132. This is the case when the alarm event data was delivered as a separate data message over the cellular network and is described in U.S. Pat. No. 8,447,265. In one embodiment, Interactive Voice Recognition (IVR) software may be used to interact with operators or to help triage users that cannot be assisted by an IVR operator.

The operator at the central station 106 manages the received call and determines if emergency response is desirable. In this regard, the operator may contact associated caregivers or responders listed in account data stored on the central station computing device 132 at the central station 106. Note that such account data may be generated and stored at the time of account creation. The caregiver or responder might include, for example, a son, daughter, friend, or neighbor of the user. The operator may also contact the corresponding Public Service Answering Point (PSAP) to dispatch local emergency response. The PSAP is the ten-digit equivalent of the "9-1-1" local exchange that is local to the monitored user 101 and is typically associated with the user account in the account data at installation time. If a caregiver or responder is unable to be reached, the central station operator may dispatch emergency medical service (EMS).

As described hereinabove, a service technician (not shown) may install the base station 103 and the wearable device 102. In this regard, the service technician installs the hardware for receiving information from the wearable device 102 and transmitting the information to the central station computing device 132 via the receiver 105. In addition, the service technician may install the wearable device 102, which may take any type of form, e.g., a wearable pendant, as described hereinabove.

In most scenarios, installation of the wearable device 102 and the base station 103 is done manually either by the monitored user 101 or the service technician (hereinafter the installer). In order to ensure that the system 100 is working properly, the system 100 in accordance with an embodiment of the present disclosure may self test. Notably, self test systems and methods described further herein are applicable to the system 100.

Typically, the installer actuates an emergency button/help button 120 on the wearable device 102 (hereinafter the "emergency button"). The wearable device 102 transmits data indicative of an alarm event to the base station 103. In response, the base station 103 transmits data through the network 104 to the receiver 105 indicating an alarm event has occurred. The receiver 105 transmits the data to the call center computing device 132 and connects the call to the first available central station operator (not shown). The installer then notifies the operator that this is a test of the system 100, and the successfully placed call indicates that the various components of the system 100, e.g., the wearable device 102 and/or the base station 103, have been properly installed. This approach has the disadvantage that it requires a live operator to test the call for a minute or more, tying up resources at the central station.

Note that in the system 100, communication protocols may be limited due to the nature of the network 104 being a PSTN. In this regard, the communication connection between the base station 103 and the receiver 104 are telephone lines (not shown).

As will be described further herein with reference to FIG. 2, the base station 103 may be a cellular base station in one embodiment, which may allow more robust communication. Further note, however, modifications to PSTN protocols may enable the afore-described method to be employed in system 100.

Figure 2:
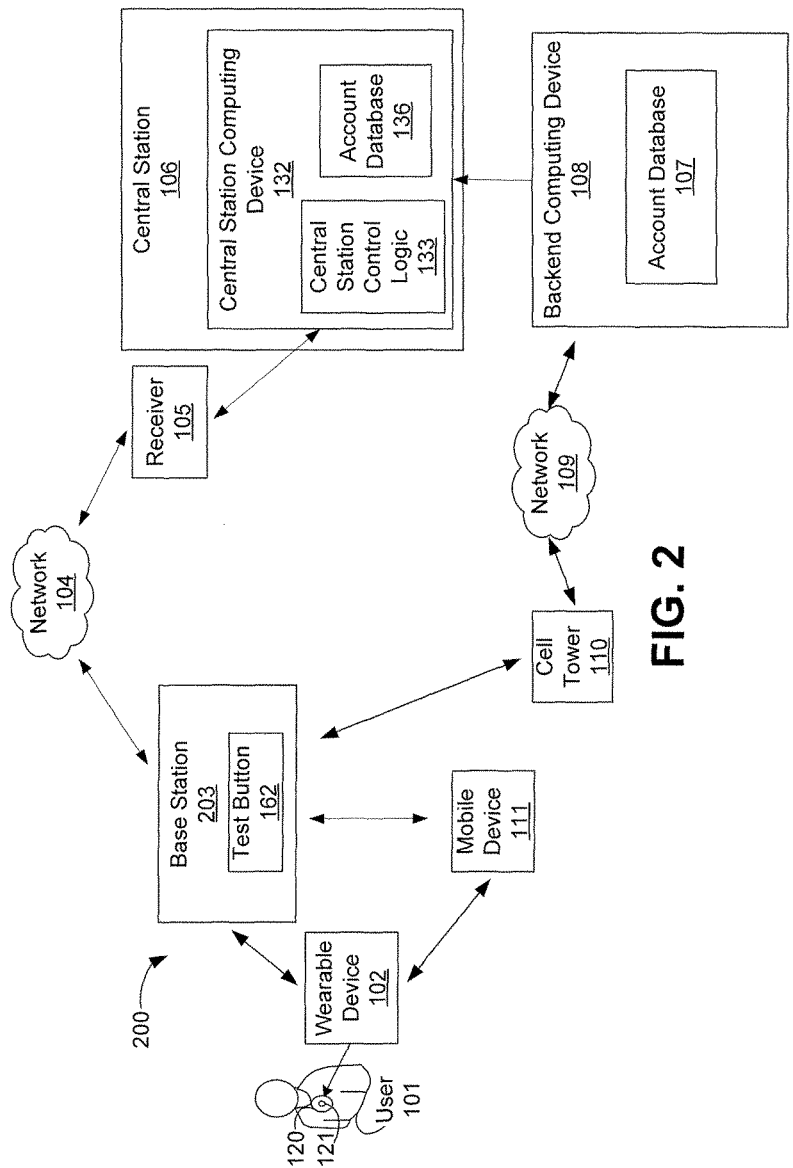
FIG. 2 is a block diagram depicting another exemplary cellular personal emergency response system (PERS) in accordance with an embodiment of the present disclosure.

FIG. 2 depicts another exemplary PERS 200 in accordance with another embodiment of the present disclosure. Such system 200 is similar to the system disclosed in U.S. Pat. No. 8,086,250, entitled Communications Method, which is fully incorporated herein by reference in its entirety.

In addition to the functionality described hereinabove, the system 200 further enables mobile device monitoring and cellular base station monitoring. In this regard, a physical wire need not exist that connects the base station 103 (FIG. 1) with the PSTN network 104 (FIG. 1), which is described further hereinabove.

In addition to the wearable device 102, described hereinabove with reference to FIG. 1, the system 200 comprises a base station 203, a mobile device 111, a cell tower 110, a network 109, and a backend computing device 108. Note that the base station 203 also comprises a test button 162, which is described further herein. The backend computing device 108 is described further with reference to FIG. 5. Note, however, that the backend computing device 108 comprises an account database 107. Further, the backend computing device 108 communicates with the central station computing device 132, and in response, the central station control logic 133 may dispatch a call or assistance to the monitored user 101 identified by the data received in the alarm. Note that throughout the remainder of the present disclosure, the term "equipment" may be used to collectively refer to any and all equipment that is installed, for example at a monitored user's residence or on the monitored user 101, in order to effectuate the system 200. In this regard, for example, the term "equipment" may collectively refer to the base station 203, the mobile device 111, and/or the wearable device 102. System 200 provides two routing paths for communication, including alarms, from the user 101 to the central station 106. In this regard, the wearable device 102 may wirelessly communicate with the cellular base station 203, which transmits data indicative of an alarm via the cell tower 110, the network 109, and the back end computing device 108. Additionally, the wearable device 102 may wirelessly communicate with the mobile device 111, which transmits data similarly via the cell tower 110.

The mobile device 111 may be, for example, a dedicated appliance, a cellular telephone, a personal digital assistant (PDA), or a computing tablet. The mobile device 111 may be any type of mobile device now known or future-developed that comprises a wireless communication device (e.g., a transceiver) or any other device capable of communicating over the cell tower 110 and/or with the base station 203.

When the monitored user 101 is within radio communication distance with the base station 203, the wearable device 102 can communicate wirelessly with the base station 203. In addition, however, the wearable device 102 may also communicate with the mobile device 111, as described hereinabove. Such communication may be simultaneous or in the alternative. Thus, if the monitored user 101 moves too far from the base station 203 for communication to occur with the base station 203, the monitored user's device 102 may still be able to transmit an alarm through the user's mobile device 111 if the user, for example, moves to a location outside the communication area of the base station 203, e.g., the monitored user 101 is located down the street or at the grocery store. The dual communication paths mitigate the risk that the user is not in constant communication with the base station 103.

In one embodiment, the base station 203 and the mobile device 111 may each receive data indicative of a single alarm from the wearable device 102. In such a scenario, the mobile device 111 may transmit data to the base station 203 to determine if the base station 203 received the same data regarding the alarm. In response, the base station 203, if active, transmits confirmation data back to the mobile device 111 indicating that the base station 203 is in range. If the mobile device 111 receives confirmation data from the base station 203, the mobile device 111 would still send data indicative of the alarm to the backend computing device 108 but include a qualifier indicating that this may be a duplicate alarm event. Such an indicator allows the backend computing device 108 to present only one of these alarms to the central station computing device 132.

The mobile device 111 communicates via the cell tower 110 and network 109 with the backend computing device 108, which is described further herein. Note that the mobile device 111 may comprise various devices for effectuating a number of functionalities, which are described further herein with reference to FIG. 5. As mere examples, the mobile device 111 may comprise a global positioning system (GPS) receiver and/or a wireless wide area network (WAN) communication device, such as a cellular radio.

The account database 107 is similar to the account database 136 of the central station computing device 132. In one embodiment, the account database 136 and the account database 107 are periodically synced so that they are substantially and effectively mirror images. In this regard, the account database 107 comprises data related to a plurality of monitored users 101 (FIG. 2). For example, the account database 107 comprises data indicative of a user's name, address, account number, and contact numbers, including mobile and landline numbers (hereinafter referred to as "account data"). In one embodiment, unique identifiers identifying equipment installed for operation for the monitored user 101 may also be stored in the account database 107. The unique identifier information may be stored prior to installation by a monitored user 101 or installer or it may be automatically populated upon connection by the base station 203 with the backend computing device 108, which is described further herein with reference to FIG. 6. In another embodiment, account database 107 and account database 136 could be the same database accessible to both the central station computing device 132 and the backend computing device 108. In such an embodiment, synchronization of the databases would not be needed.

Note that if an alarm is responded to by the central station 106, response can be noted in the account database 136. Further, receipt of the alarm signal through the backend computing device 108 may be noted in the account database 107. When synchronization occurs, the account database 107 may note, in conjunction with notation of the received alarm data, that the alarm was responded to based upon data synchronized from the account database 136.

The cell tower 110 may be any cell tower that is within a cellular network that receives and transmits data from/to mobile devices, e.g., cellular phones. In one embodiment, the network 109 is the Internet.

In one embodiment of the system 200, the wearable device 102 transmits substantially similar data in the same format whether the wearable device 102 is within the communication reach of the base station 203 or the mobile device 111. In this regard, the wearable device 102 uses a substantially identical wireless transmission scheme regardless of the equipment, e.g., the base station 203 or mobile device 111, with which it is communicating.

In one embodiment, the base station 203 is a cellular base station that communicates directly with the cell tower 110. In such an embodiment, the base station 203 may not be directly connected to the network 104, which may be a PSTN. Instead, the base station 203 comprises a radio transceiver (not shown) for communicating with the cell tower 110.

Note that when the base station 203 is being used as described with reference to FIG. 1 without mobile functionality, the base station 203 may be replaced with a cellular base station 203 to add mobile functionality as shown in FIG. 2. In this regard, when the base station 203 is a cellular base station, the system 200 may be implemented where no standard telephone line exists, for example when a voice over internet protocol (VoIP) phone line is used or a cell phone is the only phone in the residence. Furthermore, the base station 203 can communicate over the cellular data network, allowing additional information to be conveyed to the back end system 108.

Figure 3:
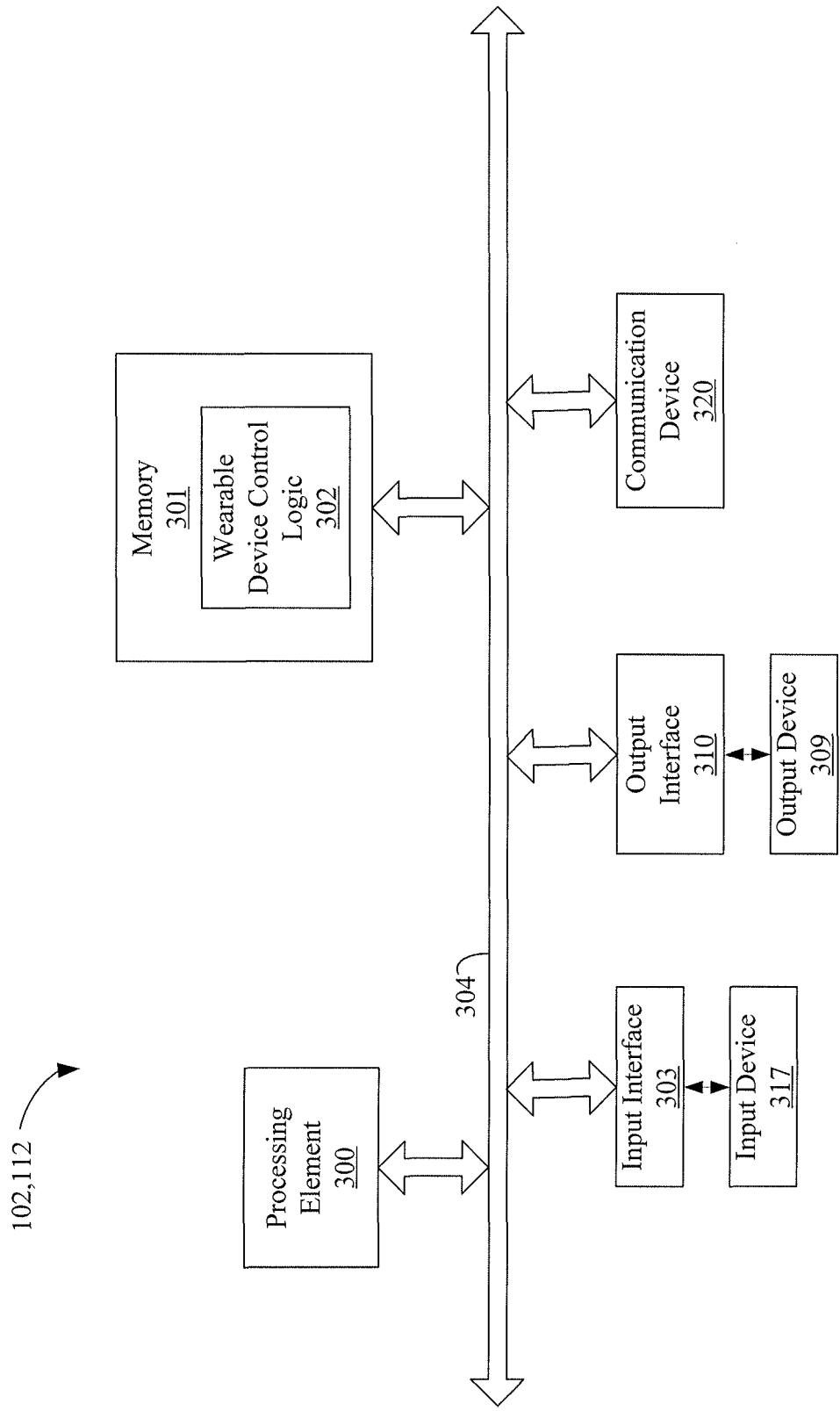
FIG. 3 is a block diagram illustrating an exemplary configuration of the wearable device depicted in FIG. 2.

FIG. 3 is a block diagram illustrating exemplary wearable devices 102, 112 for implementation in the system 200 (FIG. 2). The wearable devices 102,112 comprise wearable device control logic 302, an input interface 303, and output interface 310, and a communication device 320. In addition, the wearable devices 102, 112 comprise at least one conventional processing element 300, such as a digital signal processor (DSP) or a central processing unit (CPU), which executes programs, performs data manipulations, controls operations, and otherwise communicates with and drives the other elements within the wearable devices 102, 112 via a local interface 304, which can include at least one bus.

The control logic 302 is configured to operate the wearable devices 102, 112. The control logic 302 may be implemented in hardware, software, or a combination thereof. In FIG. 3, the control logic 302 is illustratively shown as being implemented in software and stored within the memory 301. Note that when at least a portion of the control logic 302 is implemented in software, the processing element 300 is configured to execute instructions of the control logic 302. Further note that the control logic 302, when implemented in software, can be stored and transported on any computer-readable medium for use by or in connection with an instruction execution system, apparatus, or device, such as a computer-based system, processor-containing system, or other system that can fetch and execute instructions. In the context of this document, a "computer-readable medium" can be any means that can contain, store, communicate, propagate, or transport a program for use by or in connection with the instruction execution system, apparatus, or device. The computer readable-medium can be, for example but not limited to, an electronic, magnetic, optical, electromagnetic, infrared, or semiconductor system, apparatus, device, or propagation medium. Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The input interface 303 enables a monitored user 101 to input information to the wearable devices 102,112 via an input device 317. An exemplary input device 317 is the emergency button on the belt or pendant as described hereinabove.

The output interface 310 enables a monitored user 101 to receive information from the wearable devices 102,112 via an output device 309. An exemplary output device 309 may be, for example, a speaker that delivers beep codes to the monitored user 101 or an LED indicator that flashes.

The communication device 320 allows data to be transmitted and/or received between the wearable devices 102, 112 and the base station 203 and the mobile device 111. The communication interface 320 may be any type of communication interface known in the art and/or future-developed from such communication.

Figure 4:
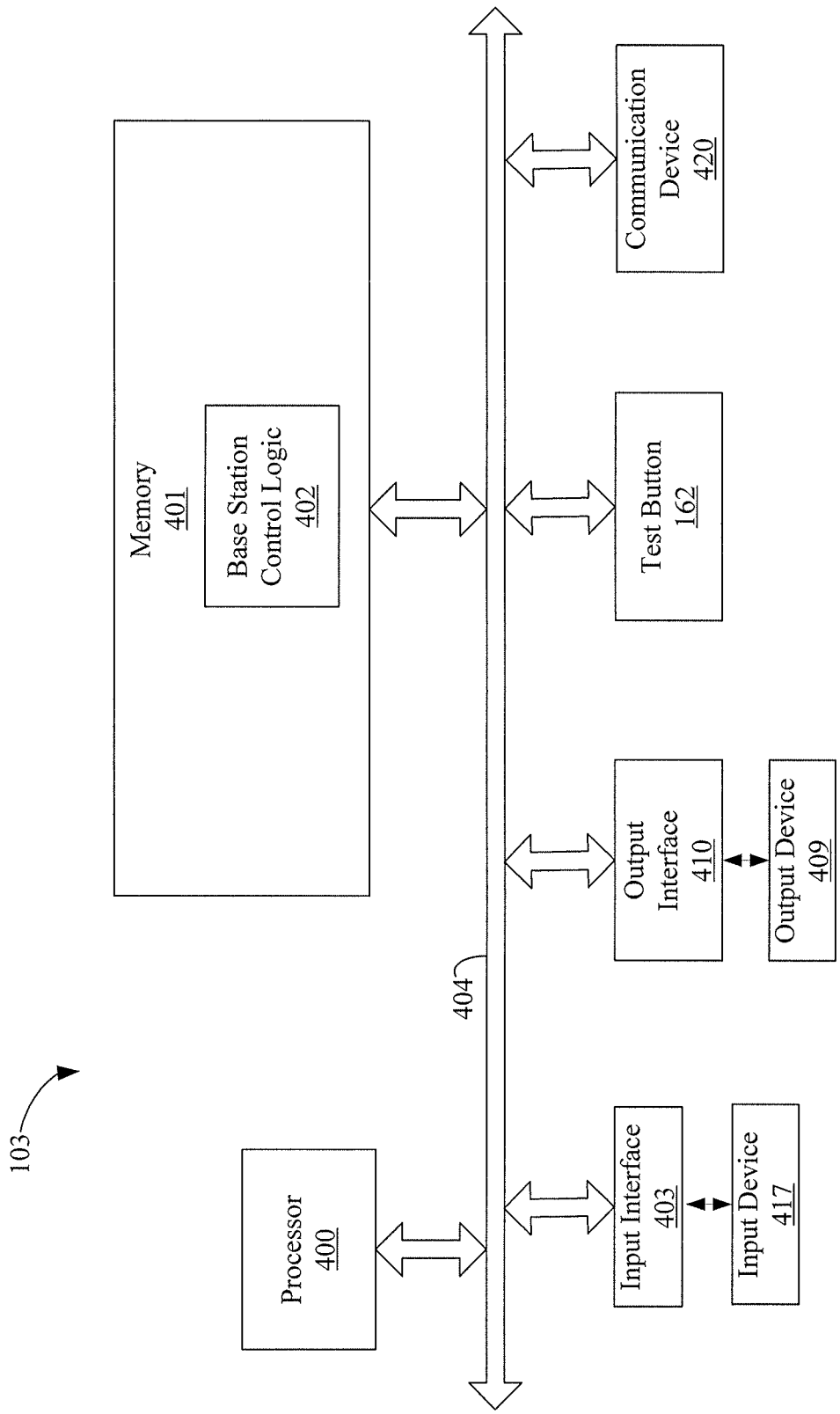
FIG. 4 is a block diagram illustrating an exemplary configuration of the base station depicted in FIG. 2.

FIG. 4 is a block diagram illustrating an exemplary base station 203 for implementation in the system 200 (FIG. 2). The base station 203 comprises base station control logic 402, an input interface 403, an output interface 410, a test button 162, and a communication device 420. In addition, the base station 203 comprises at least one conventional processing element 400, such as a digital signal processor (DSP) or a central processing unit (CPU), which executes programs, performs data manipulations, controls operations, and otherwise communicates with and drives the other elements within the base station 203 via a local interface 404, which can include at least one bus.

The base station control logic 402 is configured to operate the base station 203. The control logic 402 may be implemented in hardware, software, or a combination thereof. In FIG. 4, the control logic 402 is illustratively shown as being implemented in software and stored within the memory 401. Note that when at least a portion of the control logic 402 is implemented in software, the processing element 400 is configured to execute instructions of the control logic 402.

The input interface 403 enables a monitored user 101 or an installer (not shown) to input information to the base station 203 via an input device 417. An exemplary input device 417 may be, for example, a keyboard, keypad, or an emergency button, i.e., a button that is selectable by the monitored user 101.

The output interface 410 enables a monitored user 101 or installer (not shown) to receive information from the base station 203 via an output device 409. An exemplary output device 409 may be, for example, a display device that displays information or a speaker that provides voice commands or alarm tones of the user.

The communication device 420 allows data to be received and transmitted between the base station 203 and the mobile device 111 (FIG. 2), the network 104, and/or the wearable device 102.

In this regard, the communication device 420 may be, for example, a modem that connects the base station 203 to the network 104 and/or a radio transceiver that communicatively couples the base station 203 with the mobile device 111 and/or the wearable device 102. These are exemplary devices, and any type of communication device known in the art or future-developed may be used to communicatively couple the base station 203 with the network 104, the mobile device 11, and the wearable device 102.

The test button 162 is actuated by a user 101 or installer (not shown) upon installation of the system 200 (FIG. 2), in order to place the base station 203 in test mode. In this regard, test mode may mean that when the base station 203 transmits data, e.g., data indicative of a flag that indicates that any data transmitted therewith is test data, the receiving computing device, e.g., backend computing device 108 or the central station computing device 132, treats the incoming data as test data and responds accordingly. For example, instead of an operator being contacted to reach the user 101, as would occur in an actual emergency, other operations may be performed, as described further herein.

Figure 5:
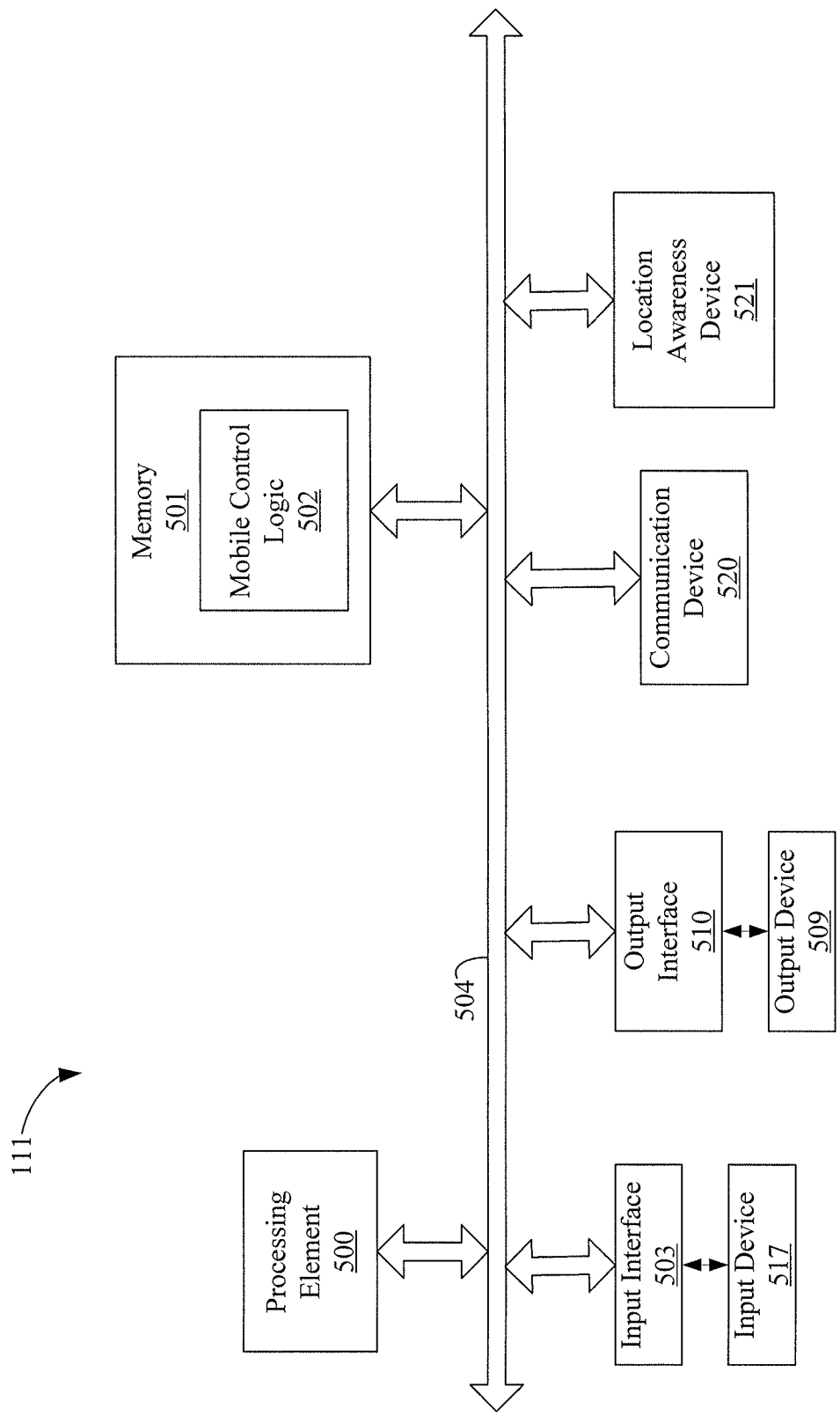
FIG. 5 is a block diagram illustrating an exemplary configuration of the mobile device depicted in FIG. 2.

FIG. 5 is a block diagram illustrating an exemplary mobile device 111 for implementation in the system 200 (FIG. 2). The mobile device 111 comprises backend control logic 502, an input interface 503, an output interface 510, and a communication device 520. In addition, the mobile device 111 comprises at least one conventional processing element 500, such as a digital signal processor (DSP) or a central processing unit (CPU), which executes programs, performs data manipulations, controls operations, and otherwise communicates with and drives the other elements within the mobile device 111 via a local interface 504, which can include at least one bus.

The backend control logic 502 is configured to operate the mobile device 111. The backend control logic 502 may be implemented in hardware, software, or a combination thereof. In FIG. 5, the backend control logic 502 is illustratively shown as being implemented in software and stored within the memory 501. Note that when at least a portion of the backend control logic 502 is implemented in software, the processing element 500 is configured to execute instructions of the backend control logic 502.

The input interface 503 enables a user (not shown) to input information to the mobile device 111 via an input device 517. An exemplary input device 617 may be, for example, an emergency button, a touch screen, or keypad.

The output interface 510 enables the monitored user 101 to receive information from the mobile device 111 via an output device 509. An exemplary output device 509 may be, for example, a display that displays information to the user.

The communication interface 520 allows data to be communicated between the mobile device 111 and the base station 203, the wearable device 102, and/or the cell tower 110 (FIG. 2). Thus, in an exemplary embodiment, the communication interface 520 may comprise, for example, a wireless transceiver (not shown) for communication with the base station 203, the wearable device 102, and the cell tower 110.

In addition, the mobile device 111 comprises a location awareness device 521. In one embodiment, the location awareness device 521 is a global positioning system (GPS) that determines the location of the mobile device 111.

During operation, the wearable device control logic 302 (FIG. 3) transmits data indicating an event has occurred to the mobile device 111. The backend control logic 502 determines if an existing alarm is currently in progress, similar to when the base station 203 receives a signal indicating an event, e.g., the monitored user 101 actuates the emergency button 120. If no alarm is currently in progress, the backend control logic 502 provides audible and visual indication to the user that an alarm is active and then obtains its current location using the location awareness device 521. Note that the location of the mobile device may be obtained in real-time, using the last known location, or some other location based service.

The backend control logic 502 transmits the data indicative of the event and location to the backend computing device 108 via the cell tower and/or via the network 109. The backend computing device 108 will then present the alarm event data with location data to the central station control logic 133. The location information enables an operator at the backend computing device 108 to send help to the user's location and access the nearest Public Service Answering Point (PSAP). Note that the user's location can be determined in real-time when an emergency event is detected or the base station 203 or mobile device 111 can periodically poll for user location and maintain data indicative of the user's last known location resident in memory 401 (base station) or 501 (mobile device), which can be used (if the poll frequency is often enough). In another embodiment, the backend computing device 108 may use the location data to identify the nearest PSAP before presenting the alarm data to the central station computing device 132. In this fashion, the alarm data would also include the 10-digit PSAP identifier.

The protocol employed to transmit data to the backend computing device 108 may be any type of protocol known in the art or future-developed. In one embodiment, the protocol is a text-based protocol using standard Internet protocols such as transmission control protocol/internet protocol (TCP/IP). An example payload message is illustrated below:

<IMSI>|<GPS Data>|ALERT|EP|1|||, where IMSI is a Unique identifier assigned when a SIM card of the mobile device 111 is activated. The unique identifier uniquely identifies the monitored user 101 to the operator (or to automated software) at the central station 106. GPS Data is data contained in the message that identifies longitude and latitude coordinates; ALERT is data contained in the message that identifies an emergency alarm; and EP is data contained in the message that identifies the type of alarm (e.g., Emergency Pendant press). This represents just one exemplary format for encoding a message and is not limited in any way by the use of other methods for transmission.

Figure 6:
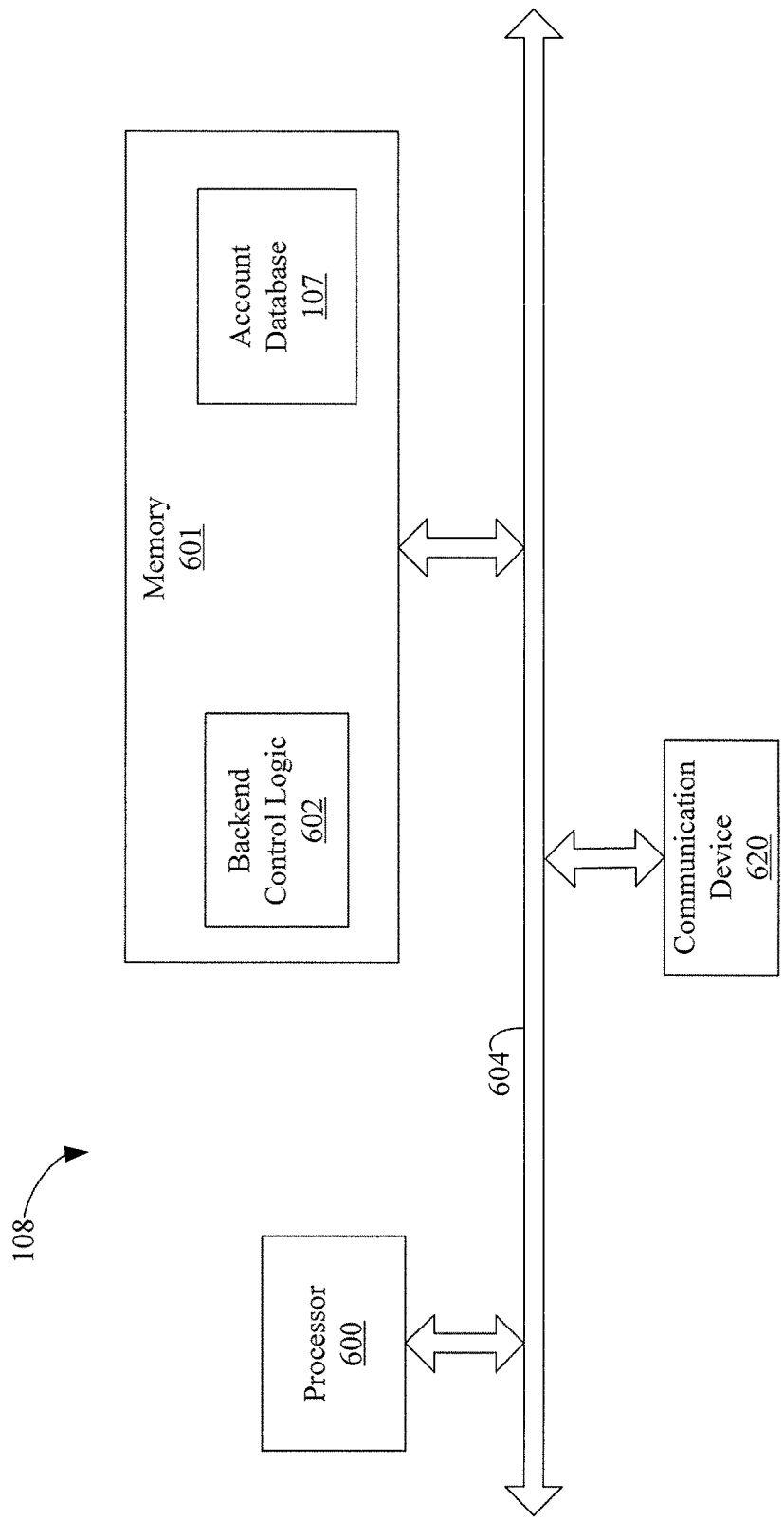
FIG. 6 is a block diagram illustrating an exemplary configuration of the backend computing device depicted in FIG. 2.

FIG. 6 is a block diagram illustrating a backend computing device 108 for implementation in the system 200 (FIG. 2). The backend computing device 108 comprises backend control logic 602 and a communication device 620. In addition, the backend computing device 108 comprises at least one conventional processing element 600, such as a digital signal processor (DSP) or a central processing unit (CPU), which executes programs, performs data manipulations, controls operations, and otherwise communicates with and drives the other elements within the backend computing device 108 via a local interface 604, which can include at least one bus.

The backend control logic 602 is configured to operate the backend computing device 108. The control logic 602 may be implemented in hardware, software, or a combination thereof. In FIG. 5, the control logic 602 is illustratively shown as being implemented in software and stored within the memory 601. Note that when at least a portion of the control logic 602 is implemented in software, the processing element 600 is configured to execute instructions of the control logic 602.

The communication interface 620 allows data to be received and transmitted to/from the backend computing device 108 between the backend computing device 108 and the network 109, which may be the Internet as described hereinabove.

Figure 7:
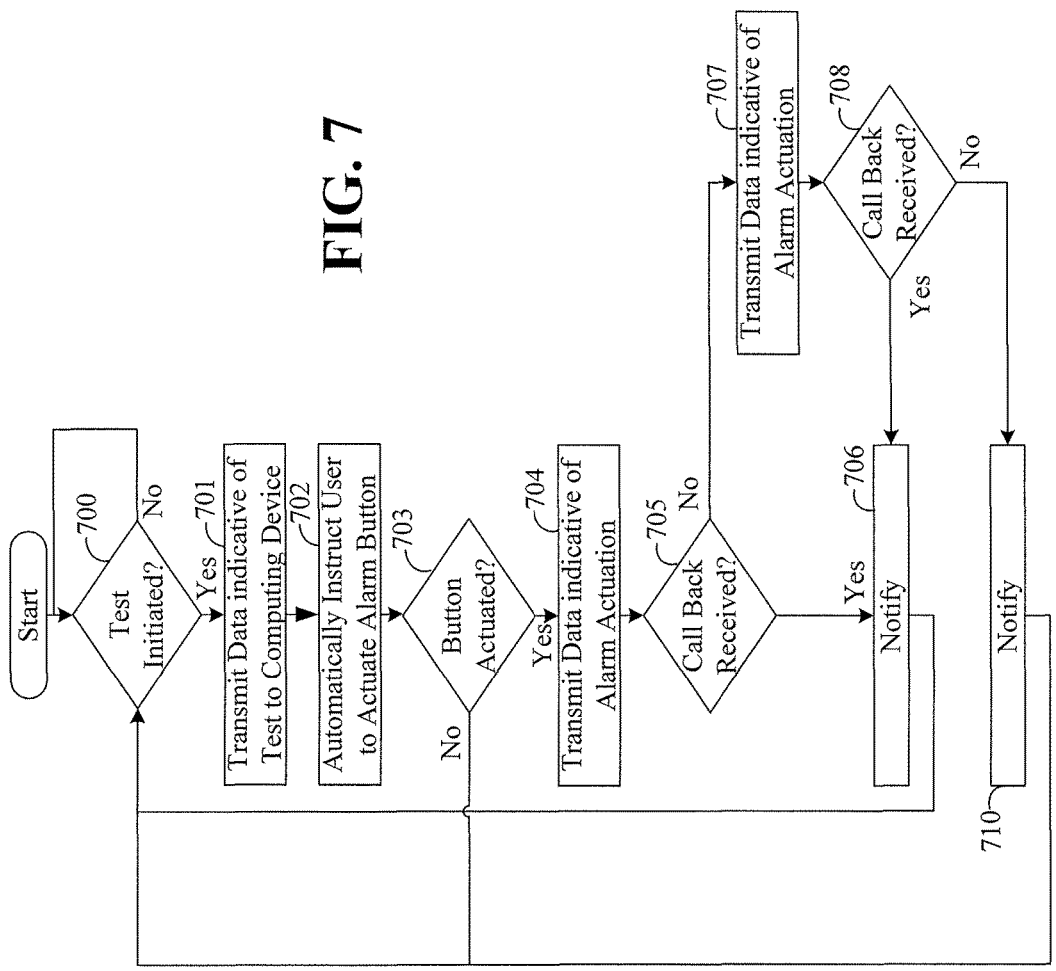
FIG. 7 is a flowchart depicting exemplary architecture and functionality of base station logic depicted in FIG. 4.

FIG. 7 is a flowchart depicting exemplary architecture and functionality of the self test methods contained within and contained in the base station control logic 402 (FIG. 4). Note that the architecture and functionality is described hereinafter with reference to the base station control logic 402; however, the architecture and functionality described hereinafter is also applicable to logic (not shown) on the mobile device 111 (FIG. 2).

In step 700, a test of the system 200 may be initiated by the monitored user 101. The test may be initiated via actuation of the test button 162 (FIG. 2 and FIG. 4) on the base station 203 (FIG. 2). The base station control logic 402 determines if a test has been initiated in step 700, and if so, the base station 203 enters into test mode.

In one embodiment, the base station control logic 402 may automatically invoke a test. In this regard, when the equipment is powered on initially during installation, the base station control logic 402 may automatically proceed to step 701, which is described further herein.

In step 702, the base station control logic 402 instructs the monitored user 101 (FIG. 1) to actuate emergency button 120 on the wearable device 102 (FIG. 2). Upon entering test mode, the base station logic 402 may play a pre-recorded audio message, e.g., a voice message, for the monitored user 101 or installer who may be testing the system 200. The audio message may suggest that to test the equipment the monitored user 101 or installer select the emergency button 120 on the wearable device 102 to perform the test, as indicated in step 702. Thus, the base station control logic 402 may wait a predefined period of time, e.g., thirty (30) seconds, to determine if the suggested action has been taken, i.e., pressing the emergency button 120. If selection of the emergency button does not occur within the predefined period, then no action has been taken, and the logic 402 resumes at the decision step 700.

In this regard, if emergency button is actuated, as determined in step 703, the base station logic 402 transmits data, e.g., a test signal, indicative of the actuation of the emergency button to the backend computing device 108 as indicated in step 704. Because the base station 203 is in test mode, the test signal will be sent via the network 109 with a "test" flag identifier. The test flag identifies the alarm event as a test of the system 200 and may be used by the backend computing device 108 and/or central station computing device 132 to avoid involving a live operator, which will be described herein.

In step 705, the base station logic 402 listens for a call from the central station computing device 132, which may be effectuated via protocol private branch exchange (PBX) located at the central station 106. In the embodiment depicted in FIG. 2, the central station control logic 133 may place a call via the receiver 105 through the network 104.

If a call is received in step 705 from the central call station computing device 132, the call's receipt by the base station 203 indicates that the data indicative of actuation of the emergency button was received by the backend server 108 and the central station computing device 132 or an operator at the central station 106 (FIG. 2).

Thus, in step 706, the base station 203 is connected to the central station computing device 132 by way of an active voice call. An operator can confirm the voice quality, or preferably a pre-recorded voice message can be used to confirm that the call was successful, and the installer can hear the voice message. In the case of a pre-recorded announcement, this may say "Thank you for testing your medical alarm". At this point, the system 200 has demonstrated that an alarm signal initiating at wearable device 102 can be sent from the wearable device 102 to the base station 203, and the base station 203 can report that to the backend computing device 108. Additionally, the successful received call indicates that the central station computing device 132 can successfully originate a call to the base station 203, as would occur during a real emergency event.

In one embodiment, the pre-recorded message may play an audio notification that prompts the monitored user 101 or the installer for input. In this regard, it may request the monitored user's name and/or to confirm that the quality of the communication is effective. In this embodiment, particular IVR logic, e.g., hardware, software, or a combination thereof, residing on the PBX may be used to analyze the response and confirm sufficient audio quality to the central station 106 and/or the backend computing device 108.

If a call is not received in response to receiving an indicator of actuation of an emergency button, the base station logic 402 may make another attempt at contacting the backend computing device 108. In this regard, in step 707, the base station logic 402 may again transmit data indicating that an emergency button has been actuated (again with the test flag set), and in step 708, the base station logic 402 waits to receive a call from the central station computing device 132.

If a call is received from the central station computing device 132, the user 101 or installer will be notified of success in step 706. As described hereinabove, successful notification may be effectuated via a voice message transmitted from the PBX at the central station 106.

If a call is not received from the central station computing device 132, the base station logic 402 notifies the monitored user 101 and/or the installer that the test failed in step 710. In one embodiment, the base station logic 402 plays an audible failure message for the monitored user 101 or installer. In addition, the base station logic 402 may activate a visual indicator (not shown), such as, for example, a series of blinking lights. An audio message and/or blinking lights are exemplary methods for notifying the monitored user 101 and/or installer. Other notification methods may be used in other embodiments.

Note that in one embodiment, the base station 203 may comprise an "Alarm" button that may be actuated by the monitored user 101 in the event of an emergency in addition to a "Test" button on the base station 203 along with the existing "Alarm" button on the wearable device 102.

Figure 8:
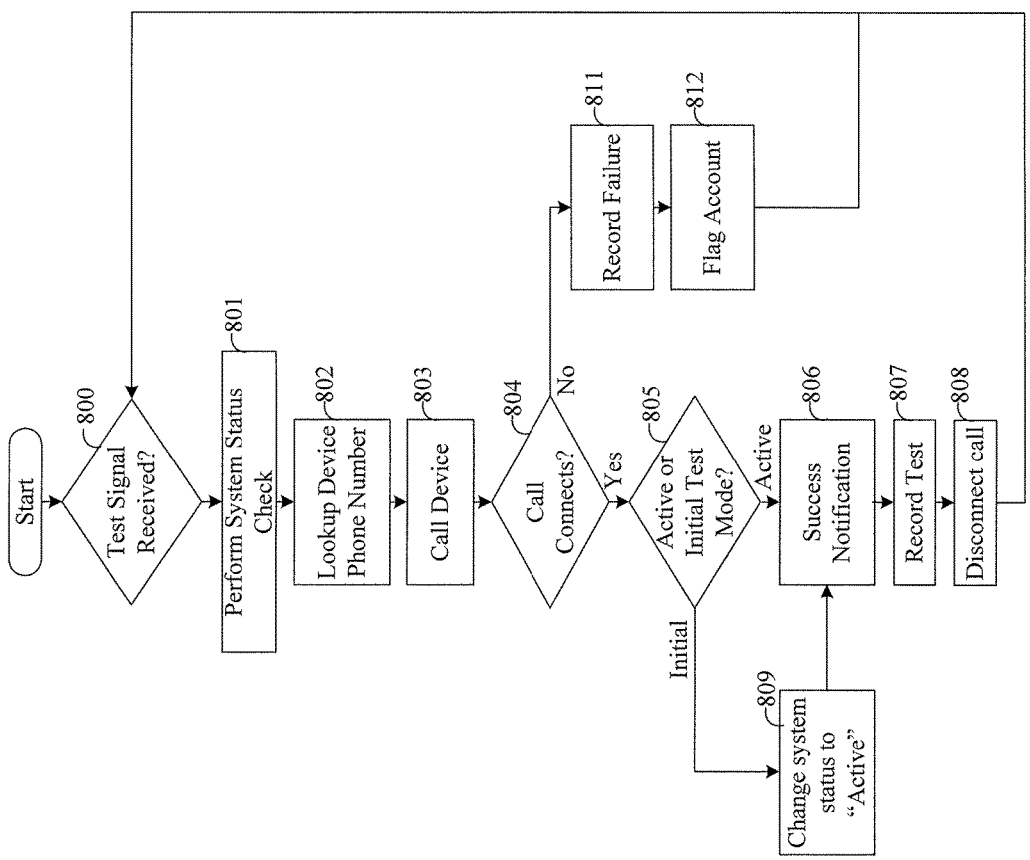
FIG. 8 is a flowchart depicting exemplary architecture and functionality of backend control logic depicted in FIG. 4.

FIG. 8 is a flowchart depicting exemplary architecture and functionality of the backend control logic 602 and the central station control logic 133 as it pertains to the self test methods (FIG. 5). Note that the architecture and functionality is described hereinafter with reference to the backend control logic 602 and the backend computing device 108 (FIGS. 2 and 5). Notably, the backend control logic 602 may be activated for a test of the system 200 where a user and corresponding base station 203 and wearable device 102 has previously been set up on the backend database 107.

In step 800, a test of the system 200 is initiated, as described hereinabove, when a monitored user 101 (FIG. 2) or installer (not shown) actuates a test button 162 (FIG. 2 and FIG. 4) on the base station 203 and subsequently presses the emergency button 120 on the wearable device 102, and the base station control logic 402 (FIG. 4) transmits data indicative of a test to the backend computing device 108.

In step 800, the backend control logic 602 awaits receipt of data indicative of a test from the base station 203. Upon receipt, the backend control logic 602 performs a system status check in step 801. In performance of the status check, the backend control logic 602 may query the account database 107 (FIG. 6) using test data received identifying the user or equipment that initiated in step 802. Step 802 confirms that the user's account and all subscriber information is correctly configured in the system and looks up the corresponding telephone number to originate a call.

In step 803, the backend control logic 602 transmits data to the central station computing device 132, and the central station control logic 133 places a call to the phone number correlated with the equipment identifiers (or the phone number identified in the message provided by the backend control logic 602) that initiated the test. In this regard, if the call does not connect, the central station control logic 133 may repeat step 803 a predefined number of time, e.g., three times. Once the predefined number of attempts fail, the central station control logic 133 records data indicative of the failure of the test initiated by the test signal received in the database 136 associated with the phone number and/or account number from which the test data was received in step 811. Note that as described hereinabove, the account databases 107 and 136 may be periodically synchronized, or in addition to recording data in the database 136, the central station control logic 133 may transmit data to the backend control logic 602, which the logic 602 may use to record such failure data in the account database 107 upon occurrence.

In one embodiment, the backend control logic 602 may automatically execute operations accordingly upon receipt of a failed test. In such an embodiment, upon the detection of a failed test, the backend control logic 602 may automatically transmit an electronic communication to a member of technical support. For example, the account database 107 may comprise data indicating a ship date and a predefined status check data, e.g., seven days from equipment ship date, on which the backend control logic 602 may electronically communicate a lack of testing on equipment that should have already been installed and tested.

Additionally, the backend control logic 602 may flag the account in the database 107 indicating that the user's equipment (e.g., the base station 203 and/or wearable device 102 associated with the user) needs service in step 812. Notably, the backend control logic 602 may further automatically notify an administrator (not shown) or an installer (not shown) that the equipment of the monitored user 101 needs service by transmitting an electronic communication, e.g., an email, a text message, a phone call, or other type of notification. In another embodiment, a user interface tool (not shown) may allow technical support staff to generate a report or list of all pending installations and new accounts that have failed the test, have not tested the equipment in given time period, or the account has failed a subsequent test. This report would allow the appropriate team to follow up and take action on such failures.

If the call connects in step 804, the central station control logic 133 may communicate such connection to the backend control logic 602. Thus, the backend control logic 602 determines whether the call was initiated in an initial setup, i.e., it is the first time the base station 203 and wearable device 102 have been activated for this particular monitored user 101, or if previously installed and setup equipment is being tested in step 805. In step 809, if the test was initiated from an initial test of equipment during installation, the backend control logic 602 changes a flag in the database 107 associated with the user's account. This account can be identified by data indicative of the monitored user's equipment from which the test data was received or by a phone number.

In one embodiment, the database record for the subscriber's account may not yet contain the hardware identifier of the equipment that is being installed. This may happen if equipment is drop shipped or installation of the equipment is fulfilled by a dealer's local inventory. In this case, the backend control logic 602 may be unable to find account data in the account database 107 corresponding to the hardware identifier. In this scenario, the backend control logic 602 may establish a call with a live operator at the central station 106 who can welcome the new user and capture name, address and other pertinent details account data that may be stored in account database 136 and/or account database 107. This data will be used to identify the user's account and then can add the hardware identifier to the database 136 and 107 on behalf of this user.

Note that in one embodiment, obtaining the user's information may be automated. In this regard, the IVR may telephone the monitored user 101 and request responses to particular questions to update or fulfill the user's account data and such responses may be stored as data in database 136 and/or 107 as provided by the monitored user 101.

In one embodiment, prior to shipping of hardware to the monitored user 101, account data is stored in the account database 107. As described hereinabove, the account database 107 may be pre-populated with unique identifiers identifying the equipment installed for the monitored user 101. The unique identifiers may be, for example, the serial numbers of the equipment. This enabled the lookup and identification of the subscriber data in step 802.

In another embodiment, the equipment identifiers need not be pre-assigned and stored in the account database 107 prior to their shipping and installation. In such an embodiment, the account data, as described hereinabove, may be stored in the account database 107 identifying pending installations or accounts that have not yet undergone an initial test and activation, which may be a subset of account data that comprises fewer entries than the account data representative of the entire subscriber base. In such a scenario, when the backend computing device 108 receives data indicative of a test, the backend computing device 108 may determine if an account is contained in the subset of account data that matches the information identified or contained in the test data. As an example, the backend control logic 502 may search the account database 107, for example, on the phone number that placed the call and transmitted the test data to identify the account data corresponding to the phone number.

Note that the determination of whether the test is from an initial setup or a preexisting or active customer may be performed in step 802 shown in FIG. 8. Further, once the determination has been made, the flag associated with the user's account may be changed at any time thereafter.

In another example, the base station 203 may comprise location awareness hardware such as global positioning (GPS) or use cellular triangulation to provide approximation of the equipment's location. It then transmits this location data in the test data identifying its location. In this example, the backend control logic 602 may search the account database 107 on the location to identify the user associated with the location. In one example, if the backend control logic 602 identifies a location in the account database 107 that is within a predefined proximity to the reported location, the backend control logic 602 may store the equipment identifiers in the account database 107 correlated with the user associated with the pending installation identified for the location. In this sense, no human interaction is needed to confirm that this new equipment being tested for the first time belongs to the subscriber associated with the pending installation.

In one embodiment, there may be a plurality of monitored user's within the subset of the account database 107 that is within the predefined proximity to the GPS location. In such a scenario, the backend control logic 602 may transmit data to the central station computing device 132 and request an operator to establish communication with the monitored user 101 or the installer to identify the user for whom the equipment is being installed.

Whether resulting from an initial test or a test from an active account, the backend control logic 602 notifies the test initiator, e.g., the monitored user 101 or an installer installing the base station 203 and/or the wearable device 102, that the test was successful in step 806. Such notification may be in the form of an audible message that is played on the base station 203, for example.

The backend control logic 502 records data indicative of the successful test in the database 107, as indicated in step 807. Thereafter, the central station computing device 132 disconnects the call in step 808.

Note that in one embodiment of the system 200, the backend computing device 108 is capable of receiving a plurality of alarms and/or test signals via multiple communication paths. For example, data indicative of a test or an alarm may be transmitted from the mobile device 111, to the cell tower 110, over the network 109 (Internet, for example), and to the backend computing device 108. Additionally, data indicative of the test or the alarm may be transmitted from the mobile device 111, to the base station 203, and to the backend computing device 108 via the network 109 or central station computing device 132 via the receiver 105. There are redundant communication paths in the system 200.

Once the account database 107 reflects data indicative of a monitored user 101, the backend control logic 602 has access data for identifying a monitored user's particular equipment. Thus, upon accessing a particular monitored user's account data in the account database 107, the backend control logic 602 may wait for a signal from each of the paths identified in the account data for the monitored user 101 that should be received from each of the identified paths. If the backend control logic 602 does not receive an alarm or test signal from one of the several communication paths for the monitored user 101 as defined in the monitored user's account data, the backend control logic 602 may transmit a notification to a system administrator that one of the various communication paths associated with the account is not operating or store data indicative of the failure in the database 107.

The backend control logic 602 may further automatically identify a possible cause of the detected fault. In this sense, the backend control logic 602 can save time by automatically isolating possible causes for the failure. This can be implemented as unique error codes for every possible error scenario combined with a lookup table indicating possible causes for each error. The table or software could also include possible actions for an administrator to take to correct the fault. In this regard, if a data indicative of a test is not received, the backend control logic 602 may identify that a subscriber identity module (SIM) card on the mobile device 111 was not activated or the monitored user 101 failed to comply with the installation and test procedures provided.

If the backend control logic 602 determines that the call placed did not connect, the backend control logic 602 may identify that the phone number provided in the account database 107 (FIG. 2) for the user's equipment was incorrectly provided. As described hereinabove, however, in some embodiments, the phone number placing the call to the backend computing device 108 may be automatically detected and/or the backend control logic 602 may also receive a hardware identifier for determining the user's phone number.

If the data in the account database 107 for the particular user identifies that a mobile device 111 is an optional path for event notification and does not receive an expected signal through such path, i.e., from the mobile device 111, cell tower 110 (FIG. 2) and over the network 109, the backend control logic 602 may identify that the mobile device may not be charged, is not in range, or its SIM card has not been activated.

If the call placed by the central station computing device 132 is answered by the base station 203 and/or the mobile device 111, the test may still not explicitly end successfully. This can be the case when the microphone at the base station is not working or the upstream talkpath is not working. In this case, IVR software prompts the user for input such as "can you hear this message clearly. If so say YES." In this regard, the backend control logic 602 may indicate that the audio is not operating at the base station 203 or the user did not comply with the instructions provided at the base station 203.

In one embodiment of the system 200, the base station 203 (or the mobile device 111) may invoke a test automatically. In this regard, the base station 203 connects to the back end computing device 108 during an initial power on sequence. The base station 203 transmits data to the backend computing device 108 to determine whether a test of the equipment is needed. If the backend control logic 602 determines that a test may be needed, e.g., the equipment contacting the backend computing device 108 is new, the backend control logic 602 may place the call to the base station 203 in response, thereby eliminating a need for an installer or a user to actuate a button to initiate a test from the wearable device 102 (FIG. 2).

While the base station 203 and backend test methods described in FIGS. 7 and 8 are in regard to a cellular system (FIG. 2), the present disclosure may be adapted for use in the system described in FIG. 1 where the base station 103 uses the network 104 to communicate with the central station computing device 132. Because no out of band data channel exists in the system 100, the base station 103 may originate a call instead of sending data in step 704 (FIG. 7). In such a case, the test signal and possibly hardware identifier could be sent in band sing dual tone multi-frequency (DTMF) tones, which is the case with alarm delivery for FIG. 1. The receiver 105 (FIG. 1) at the central station 106 (FIG. 1) and/or control logic 133 (FIG. 1) at the central station 106 is configured to interpret the received test signal and route the call to a PBX with a pre-recorded message as opposed to connecting the call to a live operator. In another embodiment, the receiver 105 may use caller identification (ID) to look up account data as opposed to using a hardware identifier.

We claim:

1. An emergency response system, comprising:
a wearable device communicatively coupled to a backend computing device via a first communication path, the wearable device configured for receiving a test input from a user and transmitting data indicative of the test input to the backend computing device via the first communication path, the data indicative of the test input comprising data identifying the first communication path;
a base station communicatively coupled to the wearable device and communicatively coupled to the backend computing device via a second communication path, the base station configured for receiving the data indicative of the test input from the user and simultaneously transmitting the data indicative of the test input over the first communication path and transmitting the data indicative of the test input over the second communication path; and
a processor resident on the backend computing device and communicatively coupled to the wearable device via the second communication path and communicatively coupled to the wearable device via the first communication path, the processor configured to receive the data indicative of the test input from the first communication path and the second communication path simultaneously, the data indicative of the test input comprising an identifier identifying the first and/or second communication path, the processor further configured for initiating a call over the first and/or second communication path as is identified in the data indicative of the test input to determine if the first and/or second communication path is operating properly thereby creating redundancy for testing communications between the wearable device and the backend computing device via the first communication path and the second communication path, the processor further configured to wait for a signal from the first communication path and the second communication path identified in memory for the user and when the processor does not receive a test signal from the first communication path and/or the second communication path, the processor transmits a notification that one or both of the first and/or second communication paths is inoperable.

2. The system of claim 1, wherein the base station comprises an actuator, and when the actuator is selected, the base station transmits the data indicative of the test input.

3. The system of claim 2, wherein the actuator is a test button adapted and arranged for selection by the user.

4. The system of claim 1, wherein the base station is configured to automatically transmit the data indicative of the test input when the base station is provided power.

5. The system of claim 1, wherein the wearable device comprises an actuator and when the actuator is selected, the wearable device transmits the data indicative of the test input to the base station.

6. The system of claim 5, wherein the base station transmits the data indicative of the test input to a backend computing device based upon receipt of the test data from the wearable device.

7. The system of claim 1, wherein the base station is configured to respond to the call initiated by the processor, the processor further configured to record data indicating status of the base station based upon the response to the call in memory.

8. The system of claim 1, further comprising a mobile device.

9. The system of claim 8, wherein the mobile device is configured to receive an input from a user initiated by the wearable device.

10. The system of claim 9, wherein the processor is further configured to initiate the call to the mobile device based upon the data indicative of the test input received from the mobile device.

11. The system of claim 10, wherein the mobile device is configured to respond to the call initiated by the processor, the processor further configured to record data in memory indicating status of the mobile device based upon the response to the call.

12. The system of claim 1, wherein the processor is further configured to determine the call to the base station has not been received and to isolate a possible cause for failure of the call.

13. The system of claim 1, further comprising a database communicatively coupled to the processor.

14. The system of claim 13, wherein the data indicative of the test input comprises data indicative of a hardware identifier.

15. The system of claim 14, wherein the processor is further configured to compare the data indicative of the hardware identifier with pre-stored account data comprising data indicative of a plurality of users and determine, based upon the comparison, if the data indicative of the hardware identifier is associated with one of the plurality of users.

16. The system of claim 15, wherein when the hardware identifier is not associated with one of the plurality of users, the processor is further configured to request, via a voice message data identifying a user.

17. The system of claim 16, wherein the processor is further configured to receive a voice response via the call in response to the voice message and store data indicative of the voice response associated with the hardware identifier in memory.

18. The system of claim 1, wherein the processor is further configured to provide, via a voice message, one or more test instructions.

19. The system of claim 1, wherein the data indicative of the test input comprises data identifying the test signal as initiating a test and the processor is further configured to automatically initiate the call based upon the data indicative of the test input.

20. The system of claim 19, wherein the processor is further configured to store data indicating results of the test correlated with data identifying the user in a memory.

21. The system of claim 20, wherein when the test is not successful, the processor is further configured to automatically notify personnel of an unsuccessful test.

22. The system of claim 1, wherein the processor is further configured to receive a voice signal from the call, analyze the integrity of the received voice signal, and determine the efficacy of the one or more communication paths based upon the analysis.

23. The system of claim 1, wherein the data indicative of the test input comprises data indicative of a location of the base station.

24. The system of claim 23, wherein the processor is further configured to compare the data indicative of the location with pre-stored account data comprising data indicative of a plurality of users and determine, based upon the comparison, the user associated with the location.

25. The system of claim 1, wherein the data indicative of the test input is a phone call originating from an identifiable phone number.

26. The system of claim 1, wherein the base station plays at least one audible installation instruction for guiding installation of the base station and wearable device.

27. The emergency response system of claim 1, wherein the first communication path comprises at least a mobile device and a cell tower.

28. The emergency response system of claim 1, wherein the second communication path comprises at least a cell tower.

29. An emergency response method, comprising:
receiving a test input from a user via a wearable device, wherein the wearable device is communicatively coupled to a backend computing device via a first communication path;
transmitting, by the wearable device, data indicative of the test input to the backend computing device over the first communication path, the data comprising an communication path identifier;
receiving from the wearable device, by the base station, the data indicative of the test input;
transmitting, by the base station, data indicative of the test input requesting a test be performed on the second communication path to the backend computing device based on the data indicative of the test input and simultaneously with the transmitting by the wearable device;
receiving the data indicative of the test input from the wearable device and the base station, wherein the data indicative of the test input indicates which of the first and/or second communication paths is to be tested; and initiating a call on the first communication path when the data indicative of the test input is received from the wearable device and initiating a call on the second communication path when the data indicative of the test input is received from the base station thereby testing the first and second communication paths simultaneously;

waiting for a signal from the first communication path and the second communication path identified in memory for the user;

when the processor does not receive a test signal from the first communication path and/or the second communication path, notifying that one or both of the first and/or second communication paths is inoperable.

30. The method of claim 29, wherein the transmitting step further comprises transmitting the data indicative of the test input in response to the user actuating an actuator.

31. The method of claim 30, wherein transmitting step further comprises actuating a test button adapted and arranged for selection by the user.

32. The method of claim 29, further comprising automatically transmitting the data indicative of the test input when the base station is provided power.

33. The method of claim 29, further comprising transmitting the data indicative of the test input to the base station from the wearable device.

34. The method of claim 33, further comprising transmitting the data indicative of the test input to a backend computing device based upon receipt of the test data from the wearable device.

35. The method of claim 29, further comprising:
responding to the call initiated; and
recording data indicating status of the base station based upon the response to the call.

36. The method of claim 29, further comprising receiving, by a mobile device, an input from a user via the wearable device.

37. The method of claim 36, further comprising initiating the call to the mobile device based upon the data indicative of the test input received from the mobile device.

38. The method of claim 37, further comprising responding by the mobile device to the call.

39. The method of claim 38, further comprising recording data in memory indicating status of the mobile device based upon the response to the call.

40. The method of claim 29, further comprising determining the call to the base station has not been received and isolating a possible cause for failure of the call.

41. The method of claim 29, wherein the transmitting the data indicative of the test input step further comprises transmitting the data indicative of the test input comprising data indicative of a hardware identifier.

42. The method of claim 41, further comprising:
comparing the data indicative of the hardware identifier with pre-stored account data comprising data indicative of a plurality of users; and
determining, based upon the comparison, if the data indicative of the hardware identifier is associated with one of the plurality of users.

43. The method of claim 42, further comprising wherein when the hardware identifier is not associated with one of the plurality of users, requesting, via a voice message, data identifying a user.

44. The method of claim 43, further comprising receiving a voice response via the call in response to the voice message and store data indicative of the voice response associated with the hardware identifier in memory.

45. The method of claim 29, further comprising providing, via a voice message, one or more installation instruction via the call.

46. The method of claim 29, wherein the initiating step further comprises when the data indicative of the test input comprises data identifying the test signal as initiating a test, automatically initiating the call based upon the data indicative of the test input.

47. The method of claim 46, further comprising storing data indicating results of the test correlated with data identifying the user in a memory.

48. The method of claim 47, further comprising when the test is not successful, automatically notifying personnel of an unsuccessful test.

49. The method of claim 29, further comprising:
receiving a voice signal from the call;
analyzing the integrity of the received voice signal; and
determining the efficacy of the one or more communication paths based upon the analysis.

50. The method of claim 29, wherein the transmitting a test signal step further requires transmitting the data indicative of the test input comprising data indicative of a location of the base station.

51. The method of claim 50, wherein the processor is further configured to compare the data indicative of the location with pre-stored account data comprising data indicative of a plurality of users and determine, based upon the comparison, the user associated with the location.

52. The method of claim 29, wherein the transmitting the data indicative of the test input step further comprises wherein the data indicative of the test input is a call originating from an identifiable phone number.

53. The method of claim 29, further comprising wherein the base station plays at least one audible installation instruction for guiding installation of the base station and wearable device.

* * * * *